(12) United States Patent
Brockbank et al.

(10) Patent No.: US 11,246,308 B2
(45) Date of Patent: Feb. 15, 2022

(54) ICE-FREE PRESERVATION OF LARGE VOLUME TISSUE SAMPLES FOR VIABLE, FUNCTIONAL TISSUE BANKING

(71) Applicant: TISSUE TESTING TECHNOLOGIES LLC, North Charleston, SC (US)

(72) Inventors: Kelvin GM Brockbank, Charleston, SC (US); Lia H. Campbell, Mount Pleasant, SC (US)

(*) Notice: Subject to any disclaimer, the term of this patent is extended or adjusted under 35 U.S.C. 154(b) by 501 days.

(21) Appl. No.: 15/843,462

(22) Filed: Dec. 15, 2017

(65) Prior Publication Data

US 2018/0192639 A1 Jul. 12, 2018

Related U.S. Application Data

(60) Provisional application No. 62/436,642, filed on Dec. 20, 2016.

(51) Int. Cl.
*A01N 1/02* (2006.01)

(52) U.S. Cl.
CPC .................. *A01N 1/0221* (2013.01)

(58) Field of Classification Search
None
See application file for complete search history.

(56) References Cited

U.S. PATENT DOCUMENTS

| | | | |
|---|---|---|---|
| 5,242,792 A | 9/1993 | Rudolph et al. | |
| 5,629,145 A | 5/1997 | Meryman | |
| 5,648,206 A | 7/1997 | Goodrich, Jr. et al. | |
| 5,827,741 A | 10/1998 | Beattie et al. | |
| 5,955,448 A | 9/1999 | Colaco et al. | |
| 5,962,214 A | 10/1999 | Fahy et al. | |
| 6,127,177 A | 10/2000 | Toner et al. | |
| 6,187,529 B1 | 2/2001 | Fahy et al. | |
| 6,194,137 B1 | 2/2001 | Khirabadi et al. | |
| 6,274,303 B1 | 8/2001 | Wowk et al. | |
| 6,395,467 B1 | 5/2002 | Fahy et al. | |
| 6,596,531 B2 | 7/2003 | Campbell et al. | |
| 6,740,484 B1 * | 5/2004 | Khirabadi ............... A01N 1/02 435/1.2 |
| 7,270,946 B2 | 9/2007 | Brockbank et al. | |
| 8,017,311 B2 | 9/2011 | Brockbank et al. | |
| 2004/0067480 A1 | 4/2004 | Brockbank et al. | |
| 2007/0190517 A1 | 8/2007 | Fahy et al. | |
| 2010/0216110 A1 | 8/2010 | Brockbank | |

(Continued)

FOREIGN PATENT DOCUMENTS

| CN | 1176738 A | 3/1998 |
|---|---|---|
| CN | 1293958 A | 5/2001 |

(Continued)

OTHER PUBLICATIONS

Da Silva et al., Pesq. Vet. Bras. 37(4): 415-423 (2017).*

(Continued)

*Primary Examiner* — Erin M. Bowers
(74) *Attorney, Agent, or Firm* — Oliff PLC

(57) ABSTRACT

Large volume cellular material may be preserved by combining the cellular material with a cryoprotectant formulation/medium/solution containing at least one sugar and then subjecting the cellular material to a vitrification preservation protocol.

20 Claims, 8 Drawing Sheets

(56) References Cited

U.S. PATENT DOCUMENTS

| | | |
|---|---|---|
| 2016/0015025 A1 | 1/2016 | Bischof et al. |
| 2017/0135335 A1 | 5/2017 | Matsuzawa et al. |
| 2017/0311587 A1 | 11/2017 | Matsuzawa et al. |

FOREIGN PATENT DOCUMENTS

| | | | |
|---|---|---|---|
| CN | 1505474 A | | 6/2004 |
| CN | 101578976 A | | 11/2009 |
| CN | 102124098 A | | 7/2011 |
| CN | 102438445 A | | 5/2012 |
| CN | 102459568 A | | 5/2012 |
| CN | 102550541 A | * | 7/2012 |
| CN | 105263320 A | | 1/2016 |
| CN | 102550541 B | | 2/2016 |
| JP | 2005-239685 A | | 9/2005 |
| JP | 2016-010359 A | | 1/2016 |
| WO | 02/32225 A2 | | 4/2002 |
| WO | 2005/027633 A2 | | 3/2005 |
| WO | 2016-063806 A1 | | 4/2016 |

OTHER PUBLICATIONS

Campbell et al., "Cryopreservation of Adherent Smooth Muscle and Endothelial Cells with Disaccharides," In: Katkov I. (ed.) Current Frontiers in Cryopreservation. Croatia: In Tech (2012).

Campbell et al., "Development of Pancreas Storage Solutions: Initial Screening of Cytoprotective Supplements for ?-cell Survival and Metabolic Status after Hypothermic Storage," Biopreservation and Biobanking 11(1): 12-18 (2013).

Taylor et al., "Comparison of Unisol with Euro-Collins Solution as a Vehicle Solution for Cryoprotectants," Transplantation Proceedings 33: 677-679 (2001).

Jul. 2, 2020 Office Action issued in European Patent Application No. 17 829 441.9.

S. Iwai et al. "Impact of Normothermic Preservation with Extracellular Type Solution Containing Trehalose on Rat Kidney Grafting from a Cardiac Death Donor." PLoS One, vol. 7, No. 3, Mar. 21, 2012, e33157 (10 pages).

G. Fahy et al. "Physical and biological aspects of renal vitrification." Organogenesis, vol. 5, No. 3, Jul. 2009, pp. 167-175.

M. Lisy et al. "The performance of ice-free cryopreserved heart valve allografts in an orthotopic pulmonary sheep model." Biomaterials, vol. 31, No. 20, Apr. 17, 2010, pp. 5306-5311.

E. Guilbert et al. "Organ Preservation: Current Concepts and New Strategies for the Next Decade " Transfusion Medicine and Hemotherapy, vol. 38, Mar. 21, 2011, pp. 125-142.

Aug. 3, 2021 Office Action issued in Japanese Patent Application No. 2019-533160.

Mar. 24, 2021 Office Action issued in Chinese Patent Application No. 201780085797.1.

Nov. 10, 2021 Preliminary Office Action issued in Brazilian Patent Application No. 112019012742-9.

Nov. 15, 2021 Office Action issued in Chinese Patent Application No. 201780085797.1.

* cited by examiner

ICE-FREE PRESERVATION OF LARGE VOLUME TISSUE SAMPLES FOR VIABLE, FUNCTIONAL TISSUE BANKING

CROSS-REFERENCE TO RELATED APPLICATION

This nonprovisional application claims the benefit of U.S. Provisional Application No. 62/436,642 filed Dec. 20, 2017. The disclosure of the prior application is hereby incorporated by reference in its entirety.

STATEMENT REGARDING FEDERALLY SPONSORED RESEARCH

This invention was made with government support under HL120404 awarded by the National Heart Lung Blood Institute of the National Institutes of Health, and W81XWH-15-C-0173 awarded by the U.S. Army Medical Research and Materiel Command Fort Detrick. The government has certain rights in the invention.

TECHNICAL FIELD

The present disclosure relates to the field of cell, tissue and organ preservation, particularly new ice-free formulations (e.g., for vitrification) incorporating sugars, such as disaccharides (e.g., trehalose and sucrose), and protocols that improve sample material properties and biological viability, even as sample volumes are increased to greater than 4 mL. More specifically, the invention relates to a method for supplementing ice-free vitrification formulations for large samples containing cellular materials (e.g., having a volume greater than 4 mL, such as greater than 10 mL) with sugars, such as disaccharides (e.g., trehalose and sucrose), in an effort to enhance cell survival and tissue functions post-preservation.

BACKGROUND

Conventional approaches to ice-free cryopreservation have been successful for storage of relatively small sample sizes. For example, human oocyte storage where it has revolutionized clinical in vitro fertilization practice.

In order for the cells or tissues to be preserved, cryoprotectant solutions are typically used to prevent damage due to freezing during the cooling or thawing/warming process. For cryopreservation to be useful, the preserved sample should retain the integrity and/or viability thereof to a reasonable level post-preservation. Thus, the process of preserving the sample should avoid and/or limit the damage or destruction of the cells and/or tissue architecture.

Vitrification, cryopreserved storage in a "glassy" rather than crystalline phase, is an important enabling approach for tissue banking and regenerative medicine, offering the ability to store and transport cells, tissues and organs for a variety of biomedical uses. In ice-free cryopreservation by vitrification the formation of ice is prevented by the presence of high concentrations of chemicals known as cryoprotectants that both interact with and replace water and, therefore, prevent water molecules from forming ice. This approach essentially stops biological time during storage below the cryoprotectant formulations glass transition temperature ($T_g$), and has been used successfully to maintain the viability and function of small-scale cell and thin tissue samples due to diffusive (heat and mass transfer) and phase change limitations that preclude use in bulk systems such as organs and larger tissues. While previous vitrification techniques (and cryoprotecting agents used therewith, such as DSMO) employing conventional boundary convection warming techniques can sometimes be successful for samples up to 4-5 mL, ice-formation still occurs as the sample volume approaches 10 mL because conventional boundary convection warming in a bath does not provide fast enough warming rates. Ice formation results in cell and tissue destruction. The major limitations of vitrification for large tissue samples are potential cytotoxicity due to prolonged exposure to the cryoprotectants employed and ice-formation during rewarming.

SUMMARY OF THE INVENTION

It was found that supplementation of ice-free vitrification formulations employed for large volume cellular materials (e.g., having a volume greater than 4 mL, such as greater than 10 mL) with sugars, such as disaccharides (e.g., trehalose and/or sucrose), resulted in increased cell survival post-preservation and tissue functions.

The present application thus provides new methodology and new formulations for treatment of large volume cellular materials in which sugars, such as disaccharides (e.g., trehalose and/or sucrose) are added to ice-free vitrification cryoprotectant formulations. Supplementation with these sugars reduces both cryoprotectant-induced cytotoxicity and the risk of ice formation during cooling and most importantly during rewarming.

DETAILED DESCRIPTION

Terminology and Definitions

Figure 1:
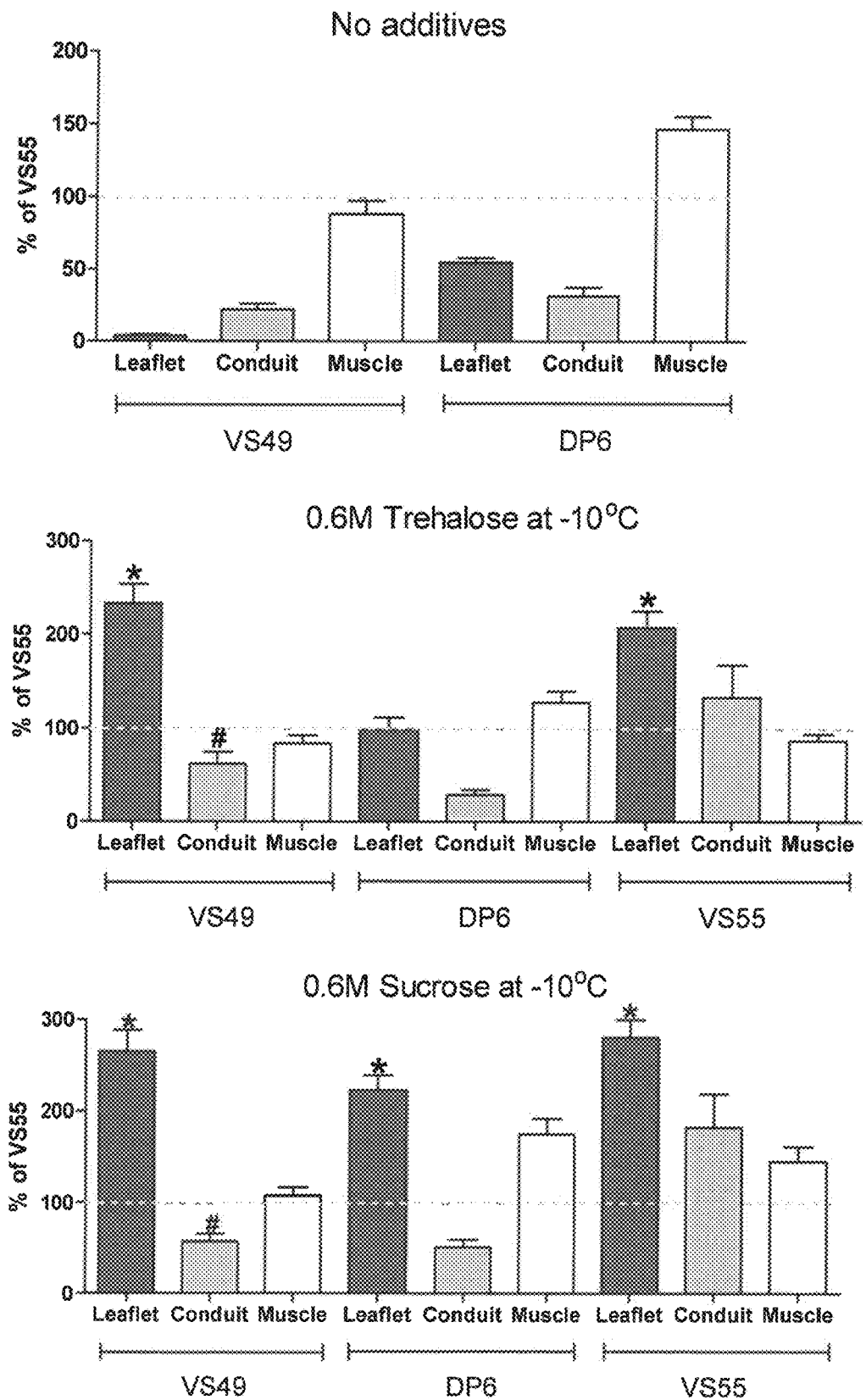
FIG. 1 is an illustration of the data obtained with respect to ice-free cryopreservation formulation supplementation experiments in which disaccharides (trehalose and sucrose) are added to various vitrification formulations (VS49, DP6, and VS55).

In the following description, numerous details are set forth to provide an understanding of the present disclosure.

However, it may be understood by those skilled in the art that the methods of the present disclosure may be practiced without these details and that numerous variations or modifications from the described embodiments may be possible.

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context.

As used herein, the term "about" used in connection with a quantity is inclusive of the stated value and has the meaning dictated by the context. For example, it includes at least the degree of error associated with the measurement of the particular quantity. When used in the context of a range, the modifier "about" should also be considered as disclosing the range defined by the absolute values of the two endpoints. For example, the range "from about 2 to about 4" also discloses the range "from 2 to 4."

Unless otherwise expressly stated herein, the modifier "about" with respect temperatures (° C.) refers to the stated temperature or range of temperatures, as well as the stated temperature or range of temperatures +/−1-4% (of the stated temperature or endpoints of a range of temperatures) of the stated. Regarding cell viability and cell retention (%), unless otherwise expressly stated herein, the modifier "about" with respect to cell viability and cell retention (%) refers to the stated value or range of values as well as the stated value or range of values +/−1-3%. Regarding expression contents, such as, for example, with the units in either parts per million (ppm) or parts per billion (ppb), unless otherwise expressly stated herein, the modifier "about" with respect to cell viability and cell retention (%) refers to the stated value or range of values as well as the stated value or range of values +/−1-3%. Regarding expressing contents with the units µg/mL, unless otherwise expressly stated herein, the modifier "about" with respect to value in µg/mL refers to the stated value or range of values as well as the stated value or range of values +/−1-4%. Regarding molarity (M), unless otherwise expressly stated herein, the modifier "about" with respect to molarity (M) refers to the stated value or range of values as well as the stated value or range of values +/−1-2%. Regarding, cooling rates (° C./min), unless otherwise expressly stated herein, the modifier "about" with respect to cooling rates (° C./min) refers to the stated value or range of values as well as the stated value or range of values +/−1-3%.

Also, in the summary and this detailed description, it should be understood that a range listed or described as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Additionally, for example, +/−1-4% is to be read as indicating each possible number along the continuum between 1 and 4. Furthermore, one or more of the data points in the present examples may be combined together, or may be combined with one of the data points in the specification to create a range, and thus include each possible value or number within this range. Thus, (1) even if numerous specific data points within the range are explicitly identified, (2) even if reference is made to a few specific data points within the range, or (3) even when no data points within the range are explicitly identified, it is to be understood (i) that the inventors appreciate and understand that any conceivable data point within the range is to be considered to have been specified, and (ii) that the inventors possessed knowledge of the entire range, each conceivable sub-range within the range, and each conceivable point within the range. Furthermore, the subject matter of this application illustratively disclosed herein suitably may be practiced in the absence of any element(s) that are not specifically disclosed herein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of concepts according to the disclosure. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

As used herein, the term "room temperature" refers to a temperature of about 18° C. to about 25° C. at standard pressure. In various examples, room temperature may be about 18° C., about 19° C., about 20° C., about 21° C., about 22° C., about 23° C., about 24° C., or about 25° C.

As used herein, "cellular material" or "cellular sample" refers to living biological material containing cellular components, whether the material is natural or man-made and includes cells, tissues and organs, whether natural or man-made. Such terms also mean any kind of living material to be cryopreserved, such as cells, tissues and organs. In some embodiments, the cells, tissues and organs may be mammalian organs (such as human organs), mammalian cells (such as human cells) and mammalian tissues (such as human tissues).

As used herein, "large volume" as used in the phrase large volume cellular material" or "large volume sample" or "large volume cellular sample" refers to living biological material containing cellular components, whether the material is natural or man-made and includes cellular materials, tissues and organs, whether natural or man-made, where such living biological material containing cellular components has a volume greater than about 4 mL, such as a volume greater than about 5 mL, or a volume greater than about 10 mL, or a volume greater than about 15 mL, or a volume greater than about 30 mL, or a volume greater than about 50 mL, or a volume greater than about 70 mL, or a volume in a range of from about 4 mL to about 200 mL, such as a volume in a range of from about 4 mL to about 50 mL, a volume in a range of from about 4 mL to about 30 mL, or a volume in a range of from about 5 mL to about 100 mL, such as a volume in a range of from about 5 mL to about 50 mL, or a volume in a range of from about 5 mL to about 30 mL, or a volume in a range of from about 6 mL to about 100 mL, or a volume in a range of from about 6 mL to about 50 mL, or a volume in a range of from about 6 mL to about 25 mL, or a volume in a range of from about 10 mL to about 100 mL, or a volume in a range of from about 10 mL to about 50 mL, or a volume in a range of from about 10 mL to about 25 mL, or a volume in a range of from about 10 mL to about 20 mL. Such terms also include any kind of living material having such a volume to be cryopreserved, such as cellular materials, tissues and organs. In some embodiments, the tissues and organs having such a volume may be mammalian organs (such as human organs), mammalian cells and mammalian tissues (such as human tissues).

As used herein, the term "organ" refers to any organ, such as, for example, liver, lung, kidney, intestine, heart, pancreas, testes, placenta, thymus, adrenal gland, arteries, veins, lymph nodes, bone or skeletal muscle. As used herein, the term "tissue" or "tissues" comprises any tissue type comprising any kind of cell type (such as from one of the above-mentioned organs) and combinations thereof, including, for example, ovarian tissue, testicular tissue, umbilical cord tissue, placental tissue, connective tissue, cardiac tissue, tissues from muscle, cartilage and bone, endocrine tissue, skin and neural tissue. The term "tissue" or "tissues" may also comprise adipose tissue or dental pulp tissue. In some embodiments, the tissue or organ is obtained from a human such as a human liver, human lung, human kidney, human intestine, human heart, human pancreas, human testes, human placenta, human thymus, human adrenal gland, human arteries, human veins, human nerves, human skin, human lymph nodes, human bone or human skeletal muscle.

As used herein, the term "cell(s)" comprises any type of cell, such as, for example, somatic cells (including all kind of cells in tissue or organs), fibroblasts, keratinocytes, hepatocytes, cardiac myocytes, smooth muscle cells, stem cells, progenitor cells, oocytes, and germ cells. Such cells may be in the form of a tissue or organ. In some embodiments, the cells are from a mammal tissue or organ, such as a human tissue or organ described above.

As used herein, "preservation protocol" refers to a process for provision of shelf life to a cell containing, living biological material. Preservation protocols may include cryopreservation by vitrification and/or anhydrobiotic preservation by either freeze-drying or desiccation.

As used herein, the term "vitrification" refers to solidification either without ice crystal formation or without substantial ice crystal formation. In some embodiments, a sample to be preserved (e.g., such as a tissue or cellular material) may be vitrified such that vitrification and/or vitreous cryopreservation (in its entirety—from initial cooling to the completion of rewarming) may be achieved without any ice crystal formation. In some embodiments, a sample to be preserved (e.g., such as a tissue or cellular material) may be vitrified such that vitrification and/or vitreous cryopreservation may be achieved where the solidification of the sample to be preserved (e.g., such as a tissue or cellular material) may occur without substantial ice crystal formation (i.e., the vitrification and/or vitreous cryopreservation (in its entirety—from initial cooling to the completion of rewarming) may be achieved even in the presence of a small, or restricted amount of ice, which is less than an amount that causes injury to the tissue).

As used herein, a sample to be preserved (e.g., such as a tissue or cellular material) is vitrified when it reaches the glass transition temperature (Tg). The process of vitrification involves a marked increase in viscosity of the cryoprotectant solution as the temperature is lowered such that ice nucleation and growth are inhibited. Generally, the lowest temperature a solution can possibly supercool to without freezing is the homogeneous nucleation temperature $T_h$, at which temperature ice crystals nucleate and grow, and a crystalline solid is formed from the solution. Vitrification solutions have a glass transition temperature $T_g$, at which temperature the solute vitrifies, or becomes a non-crystalline solid.

As used herein, the "glass transition temperature" refers to the glass transition temperature of a solution or formulation under the conditions at which the process is being conducted. In general, the methodology of the present disclosure is conducted at physiological pressures. However, higher pressures can be used as long as the sample to be preserved (e.g., such as a tissue or cellular material) is not significantly damaged thereby.

As used herein, "physiological pressures" refer to pressures that tissues undergo during normal function. The term "physiological pressures" thus includes normal atmospheric conditions, as well as the higher pressures that various tissues, such as vascularized tissues, undergo under diastolic and systolic conditions.

As used herein, the term "cryoprotectant" means a chemical that minimizes ice crystal formation in and around a tissue/organ when the tissue is cooled to subzero temperatures and results in substantially no damage to the tissue/organ after warming, in comparison to the effect of cooling without cryoprotectant.

As used herein, the term "sugar" may refer to any sugar. In some embodiments, the sugar is a polysaccharide. As used herein, the term "polysaccharide" refers to a sugar containing more than one monosaccharide unit. That is, the term polysaccharide includes oligosaccharides such as disaccharides and trisaccharides, but does not include monosaccharides. The sugar may also be a mixture of sugars, such as where at least one of the sugars is a polysaccharide. In some embodiments, the sugar is at least one member selected from the group consisting of a disaccharide and a trisaccharide. In some embodiments, the sugar is a disaccharide, such as, for example, where the disaccharide is at least one member selected from the group consisting of trehalose and sucrose. In some embodiments, the sugar is a trisaccharide, such as raffinose. The sugar may also be a combination of trehalose and/or sucrose and/or raffinose and/or other disaccharides or trisaccharides. In some embodiments, the sugar comprises trehalose.

As used herein, the term "functional after cryopreservation" in relation to a cryopreserved material means that the cryopreserved material, such as organs or tissues, after cryopreservation retains an acceptable and/or intended function after cryopreservation. In some embodiments, the cellular material after cryopreservation retains all its indented function. In some embodiments, the cellular cryopreserved material preserved by the methods of the present disclosure retains at least 50% of the intended function, such as at least 60% of the intended function, such as at least 70% of the intended function, such as at least 80% of the intended function, such as at least 90% of the intended function, such as at least 95% of the intended function, such as 100% of the intended function. For example, along with preserving the viability of the cells, it may be important to also maintain/preserve the physiological function of the tissue/organ, e.g. for a heart the pumping function, and/or the ability of a tissue (e.g., those to be transplanted) to integrate with surrounding tissue.

As used herein, the term "sterile" means free from living germs, microorganisms and other organisms capable of proliferation.

As used herein, the term "substantially free of cryoprotectant" means a cryoprotectant in an amount less than 0.01 w/w %. In some embodiments, the methods of the present disclosure may use and/or achieve a medium/solution and/or cellular material that is substantially free of cryoprotectant, such as a cellular material that is substantially free of DMSO (i.e., the DMSO is in an amount less than 0.01 w/w %). In some embodiments, the methods of the present disclosure may use and/or achieve a medium/solution and/or cellular material that is substantially free of any cryoprotectant other than the sugar, such as sucrose and/or trehalose).

EMBODIMENTS

The present disclosure is directed to methods for preserving large volume living materials/samples/organ(s)/tissue(s) (The terms "materials," "samples,", "organ(s)", and "tissue(s)" are used interchangeably and encompass any living biological material containing cellular components).

The methods of the present disclosure comprise bringing a large volume cellular material into contact with a cryoprotectant solution containing at least one sugar, such as a disaccharide (e.g., trehalose and/or sucrose). In some embodiments, this may comprise incubating a large volume cellular material in a cryoprotectant formulation/solution containing at least one sugar, such as a disaccharide (e.g., trehalose and/or sucrose) (and optionally a further cryoprotectant), such as incubating (or bringing into contact) a large volume cellular material in a medium/solution containing at least sugar, such as a disaccharide (e.g., trehalose and/or sucrose) (and optionally a further cryoprotectant). In embodiments, the at least one sugar, such as a disaccharide (e.g., trehalose and/or sucrose), may be present in the cryoprotectant formulation/solution in an amount effective to provide an environment more conducive to survival of the cells of the large volume cellular material during cooling and rewarming.

For example, in some embodiments, the cellular cryopreserved material preserved by the methods of the present disclosure retains at least 50% of the intended function, such as at least 60% of the intended function, such as at least 70% of the intended function, such as at least 80% of the intended function, such as at least 90% of the intended function, such as at least 95% of the intended function, such as 100% of the intended function. For example, along with preserving the viability of the cells in tissues and organs, it may be important to also maintain/preserve the physiological function of the cell/tissue/organ, e.g. for a heart the pumping function, and/or the ability of a tissue/cell(s) (e.g., those to be transplanted) to integrate with surrounding tissue/cell(s).

In the methods of the present disclosure, the cells of the large volume cellular material (hereinafter referred to as "cells") are protected during cryopreservation after being brought into contact with the at least one sugar, such as a disaccharide (e.g., trehalose and/or sucrose) in combination with other cryoprotectants during cooling to the cryopreservation temperature and rewarming. In embodiments, being brought into contact with the at least one sugar, such as a disaccharide (e.g., trehalose and/or sucrose) in combination with other cryoprotectants during cooling and rewarming means that the risks of ice formation is minimized such that the viability of the cells does not significantly deteriorate because the cryoprotectant solution has been stabilized/protected by the at least one sugar, such as a disaccharide (e.g., trehalose and/or sucrose) in the cryopreservation formulation/solution/composition.

In embodiments, the solution, such as a known solution well suited for organ storage of cells, tissues and organs, may contain any effective amount of sugar that is effective to provide an environment more conducive to survival of the cells of the large volume cellular material during the preservation protocol.

In some embodiments, in the methods of the present disclosure a medium (the terms "medium" and "solution" are used interchangeably) containing the at least one sugar, such as a disaccharide (e.g., trehalose and/or sucrose) in combination with other cryoprotectants may be combined with cellular materials, such as tissues and organs to prepare a cryopreservation composition. The medium (which may be an aqueous medium) can contain any suitable concentration of the at least one sugar, such as a disaccharide (e.g., trehalose and/or sucrose) in combination with other cryoprotectants for these purposes.

In some embodiments, at least one sugar, such as a disaccharide (e.g., trehalose and/or sucrose) in combination with other cryoprotectants, is used in an amount in the methods of the present disclosure such that it results in an improved viability (post-cryopreservation) of the living cellular material/sample selected from the group consisting of organs, cells and tissues, such as mammalian organs, mammalian cells, and mammalian tissues (including those which may be subsequently transplanted). The phrases, "improved cell viability" or "improved viability," refer, for example, to a cell viability (%) of at least 60%, such as 80% or more. The improved cell viability (%) may be 50% or more, 60% or more, 70% or more, 73% or more, 75% or more, 77% or more, 80% or more, 83% or more, 85% or more, 87% or more, 90% or more, 93% or more, 95% or more, 97% or more, 98% or more, or 99% or more.

In some embodiments, at least one sugar, such as a disaccharide (e.g., trehalose and/or sucrose) (and optionally a further cryoprotectant) is used in an amount in the methods of the present disclosure such that it is effective to accomplish one or more of the following: inhibit ice nucleation, modify ice structure, decrease ice formation, prevent ice formation, decrease/prevent ice formation to an extent that would allow the use of more rapid cooling rates, decrease/prevent ice formation to an extent that would allow a reduction in the amount of cryoprotectant required providing an environment more conducive to cell survival.

In some embodiments, the at least one sugar, such as a disaccharide (e.g., trehalose and/or sucrose) represents from about 1 to about 50% of the total weight of the medium comprising the cells to be preserved, such as from about 2 to about 50%, or from about 4 to about 45%, or from about 5 to 20%, or from about 5 to about 12%, or from about 6 to 20%, or from about 6 to about 12%, or from about 6 to about 10% of the total weight of the formulation/solution/medium being used with the cells to be preserved.

In some embodiments, the formulation/solution/medium contains the at least one sugar, such as a disaccharide (e.g., trehalose and/or sucrose) at a concentration ranging from 0.01 M to 5 M, from 0.1 M to 4 M, from 0.1 M to 3 M, from 0.1 M to 2 M, from 0.2 M to 2 M, from 0.3 M to 2 M, from 0.4 M to 2 M, from 0.5 M to 2 M, from 0.6 M to 2 M, from 0.1 M to 1 M, from 0.2 M to 1 M, from 0.3 M to 1 M, from 0.4 M to 1 M, from 0.5 M to 1 M, from about 0.05 M to about 6 M, about 0.1 to about 3 M, about 0.25 to about 6 M, about 0.25 to about 1 M, about 0.25 to about 2 M, about 0.25 to about 3 M, about 0.25 to about 4 M, about 0.25 to about 5 M, about 1 to about 4 M, about 1 to about 3 M, about 1 to about 2 M, about 3 to about 5 M, about 2 to about 4 M, about 0.5 to about 6 M, about 0.5 to about 5 M, about 0.5 to about 4 M, about 0.5 to about 3 M, about 0.5 to about 2 M, or about 0.5 to about 1M, wherein any concentration occurring within the above ranges can also serve as an endpoint for a range.

In embodiments, the formulation/solution/medium comprising the at least one sugar, such as a disaccharide (e.g., trehalose and/or sucrose), may be contacted with the sample to be preserved for any desired duration, such as until a desired dosage (such as an effective dosage) of the at least one sugar, such as a disaccharide (e.g., trehalose and/or sucrose) is present on/in the cells or tissues to afford an improved viability (post-cryopreservation), and/or to prevent/protect against tissue damage and/or to accomplish one or more of the following: inhibit ice nucleation, modify ice structure, decrease ice formation, prevent ice formation, decrease/prevent ice formation to an extent that would allow the use of slower cooling and warming rates, decrease/prevent ice formation to an extent that would allow a reduction in the amount of cryoprotectant required to provide an environment more conducive to cell survival to preserve tissues.

In some embodiments, the cells to be cryopreserved may also be in contact with a freezing-compatible pH buffer comprised of, for example, at least a basic salt solution, an energy source (for example, glucose), and a buffer capable of maintaining a neutral pH at cooled temperatures. Well known such materials include, for example, Dulbecco's Modified Eagle Medium (DMEM). This material may also be included as part of the cryopreservation composition. See, e.g., Campbell et al., "Cryopreservation of Adherent Smooth Muscle and Endothelial Cells with Disaccharides," In: Katkov I. (ed.) Current Frontiers in Cryopreservation. Croatia: In Tech (2012); and Campbell et al., "Development of Pancreas Storage Solutions: Initial Screening of Cytoprotective Supplements for β-cell Survival and Metabolic Status after Hypothermic Storage," Biopreservation and Biobanking 11(1): 12-18 (2013).

In some embodiments, the cryoprotectant compounds (in total, including the sugars and any other cryoprotectant) may be present in the cryopreservation composition in an amount of from, for example, about 0.05 M to about 13 M, about 0.1 to about 13 M, about 0.25 to about 13 M, about 1 to about 13 M, about 2 to about 13 M, about 4 to about 13 M, about 6 to about 13 M, about 8 to about 13 M, about 0.25 to about 11 M, about 0.25 to about 9 M, about 0.25 to about 8 M, about 0.25 to about 7 M, about 0.25 to about 10 M, about 1 to about 7 M, about 1 to about 8 M, about 1 to about 9 M, about 3 to about 10 M, about 2 to about 10 M, about 0.5 to about 10 M, about 0.5 to about 9 M, about 0.5 to about 9 M, about 0.5 to about 8 M, or about 0.5 to about 7 M, or about 6.5 to about 11 M. In some embodiments, the cryoprotectant compounds may be present in the cryopreservation composition in an amount of from, for example, about 0.05 M to about 6 M, about 0.1 to about 3 M, about 0.25 to about 6 M, about 1 to about 6 M, about 2 to about 6 M, about 3 to about 6 M, about 4 to about 6 M, about 5 to about 6M.

In some embodiments, the cellular material to be preserved may be brought into contact with a cryoprotectant-containing solution/medium/formulation/composition before, during or after incubating the cellular material to be preserved in a solution/medium/formulation/composition containing at least one sugar, such as a disaccharide (e.g., trehalose and/or sucrose). The duration that the tissue may be contacted by immersion and or perfusion in such solution/medium/formulation/composition will be a function of the mass of the tissue. In embodiments, the cooling rates of such solutions/mediums/formulations/compositions may be adjusted to provide adequate tissue permeation (function of concentration and time) to prevent ice formation.

Suitable further cryoprotectants may include, for example, acetamide, agarose, alginate, alanine, albumin, ammonium acetate, anti-freeze proteins, butanediols (such as 2,3-butanediol), chondroitin sulfate, chloroform, choline, cyclohexanediols, cyclohexanediones, cyclohexanetriols, dextrans, diethylene glycol, dimethyl acetamide, dimethyl formamide (such as n-dimethyl formamide), dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediols (such as 1,2-propanediol and 1,3-propanediol), pyridine N-oxide, raffinose, ribose, serine, sodium bromide, sodium chloride, sodium iodide, sodium nitrate, sodium nitrite, sodium sulfate, sorbitol, triethylene glycol, trimethylamine acetate, urea, valine and xylose. Other cryoprotectants that may be used in the present disclosure are described in U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 5,962,214 to Fahy et al.; U.S. Pat. No. 5,955,448 to Calaco et al.; U.S. Pat. No. 5,629,145 to Meryman; and/or WO 02/32225 A2, which corresponds to U.S. patent application Ser. No. 09/691,197 to Khirabadi et al., the disclosures of which are each hereby incorporated by reference in their entireties.

The cryoprotectant composition may also include at least one cyclohexanediol (CHD) compound, for example the cis or trans forms of 1,3-cyclohexanediol (1,3CHD) or 1,4-cyclohexanediol (1,4CHD), or racemic mixtures thereof, as a cryoprotectant compound.

The CHD compound may be present in the cryopreservation composition in an amount of from, for example, about 0.05 to about 2 M, about 0.1 M to about 1 M, about 0.1 to about 2 M, about 0.1 to about 1 M, about 0.1 to about 1.5 M, about 0.1 to about 0.5 M, about 0.1 to about 0.25 M, about 1 to about 2 M, about 1.5 to about 2 M, about 0.75 to about 2 M, about 0.75 to about 1.5 M, about 0.75 to about 1 M, about 0.05 to about 1 M, about 0.05 to about 0.75 M, about 0.05 to about 0.5 M, or about 0.05 to about 0.1 M.

The cryopreservation composition also may include (or be based on) a solution well suited for storage of cells, tissues and organs. The solution may include well known pH buffers. In some embodiments, the solution may be, for example, the EuroCollins Solution, which is composed of dextrose, potassium phosphate monobasic and dibasic, sodium bicarbonate, and potassium chloride, described in Taylor et al., "Comparison of Unisol with Euro-Collins Solution as a Vehicle Solution for Cryoprotectants," Transplantation Proceedings 33: 677-679 (2001), or a "VS55"

solution, which is an optimized cryoprotectant cocktail that has demonstrated successful vitrification of many biological systems. VS55 solution is composed of 3.1 M dimethyl sulfoxide (DMSO), 2.2 M propylene glycol, and 3.1 M formamide in a base Euro-Collins solution, for a total of 8.4M. Alternatively the cryoprotectant solution may be formulated in an alternative solution, such as Unisol.

Still further, the cryopreservation composition for use in the methods of the present disclosure may also include an anti-freeze glycolipid (AFGL), anti-freeze protein/peptide (AFP), "thermal hysteresis" proteins, (THPs) or ice recrystallization inhibitors (IRIs). Such materials may be present in the cryopreservation composition in an amount of from, for example, about 0.001 to about 1 mg/mL, about 0.05 to about 0.5 mg/mL, or about 0.1 to about 0.75 mg/mL of composition.

In some embodiments, the at least one sugar, such as a disaccharide (e.g., trehalose and/or sucrose), may act as a replacement for a cryoprotectant, such as, for example, DMSO, or as a supplement to such other cryoprotectants to reduce the concentration thereof, such as to non-toxic concentrations, at which the cryoprotectant achieves the same or better protective effects with regard to preserving as much functionality of the cryopreserved material/sample during the cryopreservation procedure. For example, in some embodiments, the at least one sugar, such as a disaccharide (e.g., trehalose and/or sucrose), may act as a replacement for a cryoprotectant, such as, for example, DMSO, in a solution known as "VS55", which is an optimized cryoprotectant cocktail that has demonstrated successful vitrification of many biological systems (VS55 solution is composed of 3.1M dimethyl sulfoxide (DMSO), 2.2M propylene glycol, and 3.1M formamide in a base Euro-Collins solution, for a total of 8.4M). In this regard, the at least one sugar, such as a disaccharide (e.g., trehalose and/or sucrose), may act as a replacement for the cryoprotectant in the VS55 solution, to reduce the concentration thereof, such as to non-toxic concentrations, or as a supplement to the other cryoprotectants in VS55 at which the cryoprotectant achieves the same or better protective effects with regard to preserving as much functionality of the cryopreserved material/sample during the cryopreservation procedure.

In some embodiments, at least one sugar, such as a disaccharide (e.g., trehalose and/or sucrose), is used in an amount in the methods of the present disclosure such that it is effective to act as a cryoprotectant for a living material/sample selected from the group consisting of organs, cells and tissues, such as mammalian organs, mammalian cells, and mammalian tissues (including those which may be subsequently transplanted).

The cells in the cellular materials that may be used in the methods of the present disclosure can be any suitable cell composition. In some embodiments, the cells can be skin cells, keratinocytes, skeletal muscle cells, cardiac muscle cells, lung cells, mesentery cells, adipose cells, stem cells, hepatocytes, epithelial cells, Kupffer cells, fibroblasts, neurons, cardio myocytes, myocytes, chondrocytes, pancreatic acinar cells, islets of Langerhans, osteocytes, myoblasts, satellite cells, endothelial cells, adipocytes, preadipocytes, biliary epithelial cells, and progenitor cells or combinations of any of these cell types.

In some embodiments, the cells used in the methods of the present disclosure may be from any suitable species of animal, for example a mammal, such as a human, canine (e.g. dog), feline (e.g. cat), equine (e.g. horse), porcine, ovine, caprine, or bovine mammal.

The formulation/composition used to prepare the cryopreservation solution can be combined with the at least one sugar, such as a disaccharide (e.g., trehalose and/or sucrose), in a variety of ways. In some embodiments, a cellular material can be combined with an aqueous liquid medium, such as an aqueous solution, containing the at least one sugar, such as a disaccharide (e.g., trehalose and/or sucrose). For example, a gradual combination, optionally with gentle agitation, can be conducted.

Once the cryopreservation composition has been prepared (and the at least one sugar, such as a disaccharide (e.g., trehalose and/or sucrose) and associated with the cellular material to be preserved), the cooling for ice-free vitrified cryopreservation may be conducted in any manner, and may use any additional materials to those described above. Protocols for preserving cellular material are described in the following patents and publications: U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 6,127,177 to Toner et al.; U.S. Pat. No. 5,962,214 to Fahy et al.; U.S. Pat. No. 5,955,448 to Calaco et al.; U.S. Pat. No. 5,827,741 to Beattie et al.; U.S. Pat. No. 5,648,206 to Goodrich et al.; U.S. Pat. No. 5,629,145 to Meryman; U.S. Pat. No. 5,242,792 to Rudolph et al.; and WO 02/32225 A2, which corresponds to U.S. patent application Ser. No. 09/691,197 to Khirabadi et al., the disclosure of which are each hereby incorporated in their entirety by reference.

The cryopreservation portion of the preservation protocol typically involves cooling cells to temperatures well below the freezing point of water, e.g., to about −80° C. or lower, more typically to about −130° C. or lower. Any method of cryopreservation known to practitioners in the art may be used. For example, the cooling protocol for cryopreservation may be any suitable type in which the cryopreservation temperature may be lower (i.e., colder) than about −20° C., such as about −80° C. or lower (i.e., colder), or about −135° C. or lower (i.e., colder). In some embodiments, the cryopreservation temperature may be in a range of from about −20° C. to about −200° C., or about −120 to about 200° C., or about −130° C. to about −196° C., or about −140° C. to about −190° C., or about −150° C. to about −190° C., or about −150° C. to about −180° C., or about −30 to about −175° C., or about −80° C. to about −160° C., or about −85° C. to about −150° C., or about −95° C. to about −135° C., or about −80° C. to about −180° C., or about −90° C. to about −196° C., or about −100° C. to about −196° C.

In some embodiments, the preservation protocol may include continuous controlled rate cooling from the point of initiation temperature (+4 to −30° C.) to −80° C. or any of the above disclosed cooling temperatures, with the rate of cooling depending on the characteristics of the cells/tissues being cryopreserved. For example, the cooling protocol for cryopreservation may be at any suitable rate, such as a rate (and/or average cooling rate, for example from the initial temperature of the sample to the cryopreservation temperature) may be greater than about −0.1° C. per minute, or greater than about −4.0° C. per minute, or greater than about −6.0° C. per minute, or greater than about −8.0° C. per minute, or greater than about −10.0° C. per minute, or greater than about −14.0° C. per minute, or greater than about −25.0° C. per minute, or greater than 50° C. per minute. The cooling rate (and/or average cooling rate), such as, for example, for continuous rate cooling (or other types of cooling), may be, for example, from about −0.1° C. to about −10° C. per minute or about −1° C. to about −2° C. per minute. The cooling rate may be about −0.1 to about −9° C.

per minute, about −0.1 to about −8° C. per minute, about −0.1 to about −7° C. per minute, about −0.1 to about −6° C. per minute, about −0.1 to about −5° C. per minute, about −0.1 to about −4° C. per minute, about −0.1 to about −3° C. per minute, about −0.1 to about −2° C. per minute, about 0.1 to about −1° C. per minute, about 0.1 to about −0.5° C. per minute, about −1 to about −2° C. per minute, about −1 to about −3° C. per minute, about −1 to about −4° C. per minute, about −1 to about −5° C. per minute, about −1 to about −6° C. per minute, about −1 to about −7° C. per minute, about −1 to about −8° C. per minute, about −1 to about −9° C. per minute, about −1 to about −10° C. per minute, about −2 to about −3° C. per minute, about −2 to about −5° C. per minute, about −2 to about −7° C. per minute, about −2 to about −8° C. per minute, about −2 to about −20° C. per minute, about −4 to about −10° C. per minute, about −4° per minute to about −8° C. per minute, about −4 to about −6° C. per minute, about −6 to about −10° C. per minute, about −6 to about −9° C. per minute, about −6 to about −8° C. per minute, about −6 to about −7° C. per minute, about −7 to about −10° C. per minute, about −7 to about −9° C. per minute, about −7 to about −8° C. per minute, about −8 to about −9° C. per minute, about −9 to about −10° C. per minute, about −7 to about −30° C. per minute, about −10 to about −25° C. per minute, about −15 to about −25° C. per minute, about −20 to about −25° C. per minute, or about −20 to about −30° C. per minute. The preservation protocol may also be independent of cooling rate in some embodiments.

Once the samples to be preserved (e.g., cellular materials and/or tissues) are cooled to about −40° C. to −80° C. or lower by this continuous rate cooling, they may be transferred to liquid nitrogen or the vapor phase of liquid nitrogen for further cooling to the cryopreservation temperature, which is typically below the glass transition temperature of the freezing solution. The samples to be preserved (e.g., cellular materials and/or tissues) may be cooled to about −40° C. to about −75° C., about −45° C. to about −70° C., about −50° C. to about −60° C., about −55° C. to about −60° C., about −70° C. to about −80° C., about −75° C. to about −80° C., about −40° C. to about −45° C., about −40° C. to about −50° C., about −40° C. to about −60° C., about −50° C. to about −70° C., or about −50° C. to about −80° C. before further cooling to the cryopreservation temperature. However, it is anticipated that the outcome is independent of cooling rate because ice formation will not occur. The limiting factor for retention of cell viability will be the duration of cryoprotectant exposure at temperatures close to zero centigrade, the lower the temperature the less the risk of cytotoxic effects until storage temperatures are achieved at which no deterioration of viability is anticipated.

The cryoprotectant formulations supplemented with sugars (such as trehalose and or sucrose) have a reduced propensity for ice nucleation during exposure to temperatures above the glass transition temperature. Thus, cellular materials in these formulation will tolerate short term exposure to temperatures such as −80° C., for minutes or hours. The precise duration depending upon the cryoprotectant/sugar formulation. The duration tolerated at each temperature will depend upon the relative cytotoxicity of the cryoprotectant formulation employed at that temperature. Furthermore, it is anticipated that these cryoprotectant formulations can be used for storage of tissues, where cell viability is not desired (some heart valves, skin, tendons and peripheral nerve grafts for example), at temperatures ranging from liquid nitrogen to physiological temperatures below the denaturation temperature range of collagen (approximately 60° C.).

Some embodiments may comprise a stepwise cooling process, in which the temperature of the tissue is decreased to a first temperature in a first solution containing cryoprotectant at a first temperature between the glass transition temperature of the first solution and −20° C., then is further decreased to a second temperature in a second solution containing cryoprotectant at temperature between the glass transition temperature of the first solution and −20° C., and this process may be repeated with a third, fourth, fifth, sixth, seventh, etc., solution until the desired temperature is achieved.

In embodiments, the glass transition temperature of the first solution (such as a cryoprotectant formulation) may be in set at any desired level, such as, for example, in a range of from about −100° C. to about −140° C., such as about −110° C. to about −130° C., or −115° C. to about −130° C. In embodiments, the tissue may be cooled and subsequently stored at temperatures between the glass transition temperature and about −20° C., such as about −120° C. to about −20° C., such as between about −110° C. to about −30° C., or between about −90° C. and about −60° C.

After being immersed in an initial solution, the sample to be preserved (such as a cellular material or tissue) may be immersed in a solution containing cryoprotectant. The final cryoprotectant concentration may be reached in a stepwise cooling process in which the sample to be preserved (such as a cellular material or tissue) may be immersed in a first solution containing a first cryoprotectant concentration, then the tissue may be immersed in a second solution containing a second cryoprotectant concentration (which is higher than the first cryoprotectant concentration), and this process may be repeated with a third, fourth, fifth, sixth, seventh, etc., solution until the desired concentration is achieved. The cryoprotectant solution may contain any combination of cryoprotectants. In some embodiments, the final desired cryoprotectant concentration may be achieved at any suitable temperature that limits the growth of ice during cooling such that ice-induced damage does not occur, for example the final desired cryoprotectant concentration may be achieved at a temperature in the range of from 0° C. to about −30° C., such as about −5° C. to about −20° C., or about −7° C. to about −15° C., or −8° C. to about −12° C., or a temperature of about −10° C.

In embodiments, the sample to be preserved (such as a cellular material or tissue) may remain free from ice and/or free from ice-induced damage during the preservation protocol (e.g., the cooling protocol, storage, and warming protocol). For example, after completion of the cooling process, the sample to be preserved (such as a cellular material or tissue) may remain free from ice and/or free from ice-induced damage during the storage step/phase for a long period of time, such as a period of at least 3 days, or a period of at least 5 days, or a period of at least 7 days, or a period of at least 8 days.

In some embodiments, upon initiation of the cooling process, the sample to be preserved (such as a cellular material or tissue) may remain free from ice and/or free from ice-induced damage during the entire preservation protocol (i.e., during the cooling protocol, storage, and warming protocol), where the entire preservation protocol (e.g., the cooling protocol, storage step/phase, and warming protocol) has a duration in a range of from at least 3 days to up to about 3 months, or a duration in a range in a range of from at least 5 days up to about 2 months, or a duration in a range in a range of from at least 7 days up to about 1 month, or a duration in a range in a range of from at least 8 days up to about 21 days, or a duration in a range in a range of from at least 8 days up to about 14 days. Additionally, in embodiments, during such preservation protocols the sample to be preserved (such as a cellular material or tissue) will experience minimal cytotoxicity during the duration of the preservation protocol.

The warming protocol may involve a two-step warming procedure (such as that described by Campbell et al., Two stage method for thawing cryopreserved cells; see, for example, U.S. Pat. No. 6,596,531, the disclosure of which is hereby incorporated by reference in its entirety. In the two-step warming protocol, the cryopreserved cellular materials (cryopreserved at the cryopreservation temperature) may be removed from the storage freezer. The cryopreserved cellular materials are allowed to first slowly warm in a first environment in the first step of the two-step protocol. The environment is not required to undergo any special treatment or have any particular make-up, and any environment may be used. The environment may be a gaseous atmosphere, for example, air. To effect the slow warming of the first stage, the environment may be at a first warming temperature greater than the cryopreservation temperature. The first warming temperature may be below freezing temperature. For example, temperatures of −30° C. or, such as about −15° C. to about −30° C., about −20° C. to about −25° C., or about −20° to about −30° C. may be used. The advantage of warming in the first step to a sub-zero centigrade temperature is that the potential cytotoxic effects of the cryoprotectant formulation at warmer temperatures will be minimized.

The second step of the two-step warming procedure involves rewarming the cellular material rapidly in a second environment at a second warming temperature that is greater than the warming temperature used in the first warming step. The second warming temperature may be 32° C. or more, about 32° C. to about 50° C., about 35° C. to about 45° C., about 40° C. to about 50° C., about 45° C. to about 50° C., about 32° C. to about 40° C., about 35° C. to about 40° C., or about 37° C. Again, any suitable environment such as gas (air), liquid, or fluid bed may be used as the second environment. For example, a water or dimethylsulfoxide bath at the warm temperature may be used to effect this rapid rewarming. During this step dilution of the cryoprotectants can be initiated using warm diluent solutions that will also contribute to the warming step.

In some embodiments, the conventional heating methods that may be used to warm the samples include, for example, convection and microwave heating. Prior to the methodology of the present disclosure, conventional methodology including convection heating, which heats from the outer boundary, is effective for small vitrified samples but ineffective for large samples (e.g., having a volume greater than 5 mL) due to cytotoxicity and ice formation. In some embodiments, low radiofrequencies and inductive heating may be used to heat when combined with distributed biocompatible magnetic nanoparticles (mNPs). See, for example, U.S. Patent Application Publication No. 2016/0015025, the disclosure of which is hereby incorporated by reference in its entirety.

In embodiments, a majority or all of the cells of the sample (e.g., tissue or cellular material) to be preserved may remain viable after the preservation protocol as the majority or all of the cells of the sample will be exposed to minimal cytotoxicity. In other words, the methods of the present disclosure avoid the cytotoxicity of some conventional cryoprotectant solutions by avoiding exposure of the sample to be preserved to the increase of cytotoxicity of the cryoprotectant solution that occurs as the tissue (and solution) temperatures approaches 37° C. In embodiments, the methods of the present disclosure avoid exposing the sample to be preserved to any conditions and/or cryoprotectants (e.g., by exposure to the extreme conditions, such as severe osmotic stresses and/or chemical cytotoxicity) that may kill a majority or all of the cells (e.g., because of the increased level of cytotoxicity of the cryoprotectant solution at temperatures approaching 37° C.) of the tissue to be preserved. However, it should be noted that in embodiments where cell viability is not desired chemical toxicity or severe osmotic stresses may be employed to render the cellular materials essentially free of living cells.

In embodiments, the cryopreserved cellular materials preserved by the methods of the present disclosure may be put to any suitable use, including, for example, research or therapeutic uses. For example, regarding therapeutic uses, the cryopreserved cellular materials may be administered to a human or animal patient to treat or prevent a disease or condition such as aortic heart disease, degenerative joint disease, degenerative bone disease, colon or intestinal diseases, degenerative myelopathy, chronic renal failure disease, heart disease, intervertebral disc disease, corneal disease, spinal trauma and replacement of parts lost due to trauma, such as fingers, limb extremities, and faces.

The cryopreserved cellular materials can be administered to a patient in any suitable manner. In some embodiments, the cryopreserved cellular materials may be delivered topically to the patient (e.g. in the treatment of burns, wounds, or skin disorders). In some embodiments, the cryopreserved cellular materials may be delivered to a local implant site within a patient. Any of these or any combination of these modes of administration may be used in the treatment of a patient.

In a first aspect, the present disclosure relates to a method for preserving living large volume cellular material, comprising: exposing the cellular material to a cryoprotectant formulation/solution/medium containing at least one sugar, subjecting the cellular material to a preservation protocol in which ice-induced damage to the cellular material does not occur, and obtaining a cryopreserved cellular material. In a second aspect the method of the first aspect may be a method in which the cellular material has a volume greater than 4 mL. In a third aspect, the method of any of the above aspects may be a method in which the volume of the cellular material is greater than 10 mL. In a fourth aspect, the method of any of the above aspects may be a method in which wherein the cellular material is ice-free for at least 7 days upon subjecting the cellular material to the preservation protocol. In a fifth aspect, the method of any of the above aspects may be a method in which the preservation protocol includes a vitrification strategy that limits the growth of ice during cooling and warming such that ice-induced damage does not occur during the preservation protocol. In a sixth aspect, the method of any of the above aspects may be a method in which the at least one sugar is a disaccharide. In a seventh aspect, the method of any of the above aspects may be a method in which the at least one sugar is selected from the group consisting of trehalose and sucrose. In an eighth aspect, the method of any of the above aspects may be a method in which subjecting the cellular material to a preservation protocol comprises: stepwise cryoprotectant addition to the cryoprotectant formulation/solution/medium to achieve a final cryoprotectant formulation/solution/medium with a cryoprotectant concentration and/or at least one sugar concentration effective to avoid ice-induced damage to the cellular material, such as where the last cryoprotectant addition step that achieves the final cryoprotectant formulation/solution/medium is performed while the cryoprotectant formulation/solution/medium is being maintained at a temperature of about −10° C. In a ninth aspect, the method of any of the above aspects may be a method in which subjecting the cellular material to a preservation protocol comprises: immersing the cellular material in a series of solutions having increasing concentrations of the cryoprotectant and/or increasing concentrations of the at least one sugar to achieve immersion in a final solution with a cryoprotectant concentration and/or at least one sugar concentration effective to avoid ice-induced damage to the cellular material. In a tenth aspect, the method of any of the above aspects may be a method in which the cellular material is incubated in a cryoprotectant formulation, the cryoprotectant formulation containing from 0.1 to 1 M of the at least one sugar. In a eleventh aspect, the method of any of the above aspects may be a method in which the preservation protocol further comprises cooling the cellular material in a cryoprotectant formulation containing at least one sugar, such as where a further cryoprotectant is added to the cryoprotectant formulation prior or during cooling, the further cryoprotectant being different from the sugar, such as where the further cryoprotectant is selected from the group consisting of acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, ice recrystalization inhibitors, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose, and, if desired, the cryoprotectant formulation may contain the further cryoprotectant at a concentration of from 0.1 to 13.0 M. In a twelfth aspect, the method of any of the above aspects may be a method in which said cellular material is a natural or man-made tissue or organ. In a thirteenth aspect, the method of any of the above aspects may be a method in which the cellular material is selected from the group consisting of mammalian organs and mammalian tissues. In a fourteenth aspect, the method of any of the above aspects may be a method in which the cellular material is selected from the group consisting of human organs and human tissues. In a fifteenth aspect, the method of any of the above aspects may be a method in which a cell viability (%) of the cellular material after completion of the preservation protocol is at least 60%. In sixteenth aspect, the method of any of the above aspects may be a method in which the medium does not contain DMSO. In a seventeenth aspect, the method of any of the above aspects may be a method in which the medium does not contain formamide. In an eighteenth aspect, the method of any of the above aspects may be a method in which wherein the medium does not contain propylene glycol. In a nineteenth aspect, the method of any of the above aspects may be a method in which the medium does not contain DMSO, formamide and/or propylene glycol.

In a further aspect, the present disclosure also relates to cryopreserved cellular material obtained by exposure of a living large volume cellular material to a cryoprotectant formulation containing at least one sugar, and optionally a further cryoprotectant, during a preservation protocol; wherein a cell viability (%) of the cellular material after the preservation protocol is at least 50%, and the cellular material has a volume greater than 4 mL, such cryopreserved cellular material may be obtained, for example, by a method of any of the above aspects, and may be administered to a patient.

In a further aspect, the present disclosure also relates to a method for increasing production yield of viable cryopreserved cellular material, comprising: exposure of a large volume cellular material to a cryoprotectant, the cryoprotectant containing at least one sugar, for a predetermined amount of time to form a cryopreservation formulation; subjecting the cryopreservation formulation to a preservation protocol comprising cryopreservation at a cryopreservation temperature of about −80° C. or lower; and after completion of the preservation protocol, recovering the cryopreserved cellular material; wherein a cell viability (%) of the recovered cryopreserved cellular material is at least 60% and the cellular material has a volume greater than 4 mL. In a further aspect, the method of any of the above aspects may be a method in which the cellular material is selected from the group consisting of organs and tissues. In a further aspect, the method of any of the above aspects may be a method in which the cellular material is selected from the group consisting of mammalian organs and mammalian tissues. In a further aspect, the method of any of the above aspects may be a method in which the cellular material is selected from the group consisting of human organs and human tissues. In a further aspect, the method of any of the above aspects may be a method in which wherein the cell viability (%) of the recovered cryopreserved cellular material is at least 80%.

In a further aspect, the present disclosure also relates to a method for storing living large volume cellular material in which cellular viability is not desired, comprising: exposing the cellular material to a cryoprotectant formulation/solution/medium containing at least one sugar, subjecting the cellular material to a preservation protocol, which comprises storing the cellular material at temperatures ranging from the temperature of liquid nitrogen to physiological temperatures below the denaturation temperature range of collagen, and obtaining a cryopreserved cellular material. In a further aspect, the method of any of the above aspects may be a method in which the cellular material is selected from the group consisting of heart valves, skin, tendons and peripheral nerve grafts. In a further aspect, the method of any of the above aspects may be a method in which the cellular material is obtained from a mammal. In a further aspect, the method of any of the above aspects may be a method in which the cellular material is obtained from a human. In a further aspect, the method of any of the above aspects may be a method in which the cellular material is stored at temperatures ranging from about −190° C. to about 60° C. In a further aspect, the method of any of the above aspects may be a method in which the cell viability (%) of the recovered cryopreserved cellular material is 0%.

The foregoing is further illustrated by reference to the following examples, which are presented for purposes of illustration and are not intended to limit the scope of the present disclosure.

EXAMPLES

1st Set of Experiments

In the following ice-free cryopreservation formulation supplementation experiments, disaccharides (trehalose and sucrose) are added to various vitrification formulations (VS49, DP6, and VS55) in the amounts shown in FIG. 1 and compared to a solution (without trehalose and/or sucrose) to access the effectiveness at inhibiting ice formation in various tissues.

In particular, the FIG. 1 shows that there are significant increases in tissue viability induced by trehalose and sucrose supplementation of vitrification formulations. Data shown in % of control VS55 results performed with the final cryoprotectant concentration added at 4° C., N=6, *p<0.05 by ANOVA or #T-test compared with no additive controls.

In this experiment, addition of either 600 mM trehalose or sucrose to VS49, DP6 and VS55 formulations was compared. The tissues were vitrified in 4 mL of solution. Trehalose supplementation increased leaflet viability in VS49 and VS55. Sucrose supplementation increased leaflet viability in all three formulations. These differences were significantly different, p<0.05 by ANOVA or T-test. DP6 consistently had the best muscle preservation in all treatment groups but did not achieve statistical significance in this experiment, however, this outcome suggested that cardiac muscle is more tolerant of ice formation than the other tissue types (leaflet and artery) and that formamide might be causing some cytotoxicity. This led to plans to test DP6 with sugars more thoroughly in later experiments. Repetitive experiments were performed using sucrose supplemented VS55 and obtained outcomes similar to those for supplemented VS55 shown here.

Methods

Heart Valve and Blood Vessel Procurement:

Bonafide excess heart valves or blood vessels were obtained from animals employed in other IACUC approved research studies or from a food processing plant postmortem. The tissues were dissected, rinsed and placed in sterile cups with ice-cold tissue culture medium containing antibiotics overnight and then allocated for in vitro studies. The heart valve tissues in FIG. 1 each consisted of a piece of tissue consisting of pulmonary artery, leaflet and cardiac muscle. They were separated and individually assayed for viability using an assay that assesses metabolic activity that is described below.

Vitrification Method:

Tissues were gradually infiltrated with VS55 consisting of 3.10 M DMSO, 3.10M formamide, and 2.21 M propylene glycol in Euro-Collins solution at 4° C. using methods previously described for blood vessel vitrification, a dilution of VS55 to VS49 or DP6 consisting of 3 M DMSO, 3 M propylene glycol. Precooled dilute vitrification solutions (4° C.) are added in five sequential 15-min steps of increasing concentration on ice. The last cryoprotectant concentration with mNPs was added in a final sixth addition step in either precooled −10° C. or 4° C. full strength vitrification solution and kept in a −10° C. bath for 15 minutes or at 4° C. on ice in plastic tubes. The samples were then cooled in two steps, first rapid cooling to −100° C. by placing in a precooled 2-methylbutane bath at −135° C. and then by transfer to vapor phase nitrogen storage for slower cooling to below −135° C. Finally, the samples were stored below −130° C. in vapor phase nitrogen for at least 24 h before testing.

Warming:

Warming was performed by either convection warming or nanowarming. Convection warming is a two-stage process including slow warming to −100° C. and then as rapid as possible warming to melting. The slow warming rate is created by taking the sample to the top of the −135° C. freezer and the control warming rate is generated by placing the plastic container in the mixture of 30% DMSO/H2O at room temperature. After rewarming, the vitrification solution was removed in a stepwise manner on ice to keep the tissues cold and minimize cytotoxicity due to the presence of residual cryoprotectants.

Viability Assessment:

Metabolic Activity—An alamarBlue™ assay will be used to evaluate the metabolic activity of control and treated tissue samples. Tissues were incubated in 2 ml of DMEM+ 10% FBS culture medium for one hour to equilibrate followed by the addition of 20% AlamarBlue under standard cell culture conditions for 3 hours. AlamarBlue is a nontoxic fluorometric indicator based on detection of metabolic activity. Fluorescence was measured at an excitation wavelength of 544 nm and an emission wavelength of 590 nm. This evaluation was performed after rewarming (day 0) to demonstrate cell viability. Control and experimental tissues were dried at the end of each experiment, weighed, and results expressed as relative fluorescence units (RFU)/mg tissue dry weight.

The results of these experiments indicate that 0.6M of trehalose or sucrose prevents visible ice formation in both DP6 and VS49 formulations and increases post-vitrification viability in these solutions (DP6, VS49 and VS55) with leaflet viability demonstrating 2-3 fold increases. Notably, the VS49 or DP6 formulations are not effective at controlling ice formation using conventional convection warming, described in U.S. Patent Application Publication No. 2016/ 0015025. However, no ice formation was observed in the presence of either trehalose or sucrose during cooling and rewarming in these experiments with nanowarming.

2nd Set of Experiments

Figure 2:
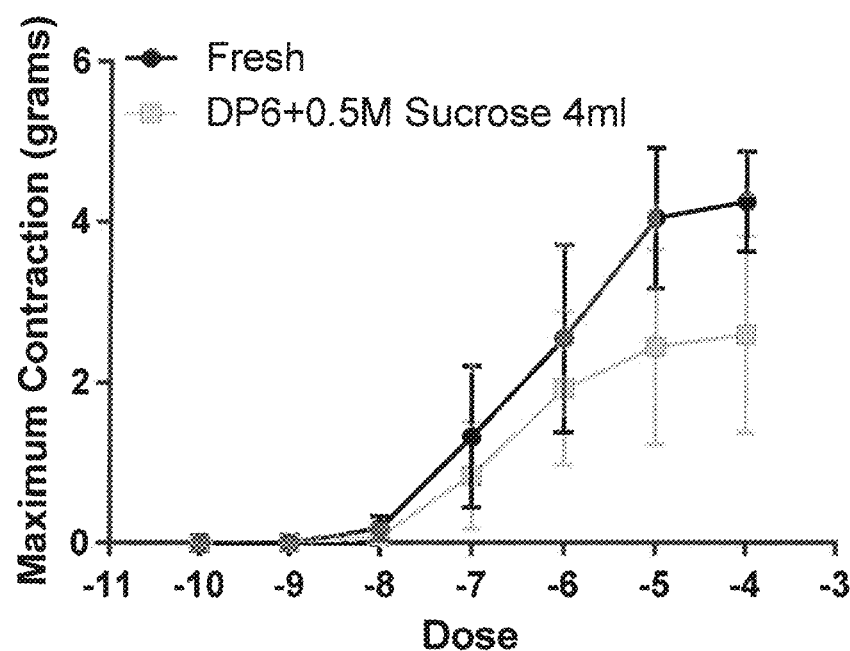
FIG. 2 is an illustration of the data obtained with respect to contractile responses of fresh and vitrified rabbit carotid arteries, (top) Norepinephrine and Phenylephrine (lower) dose response curves.
Figure 2:
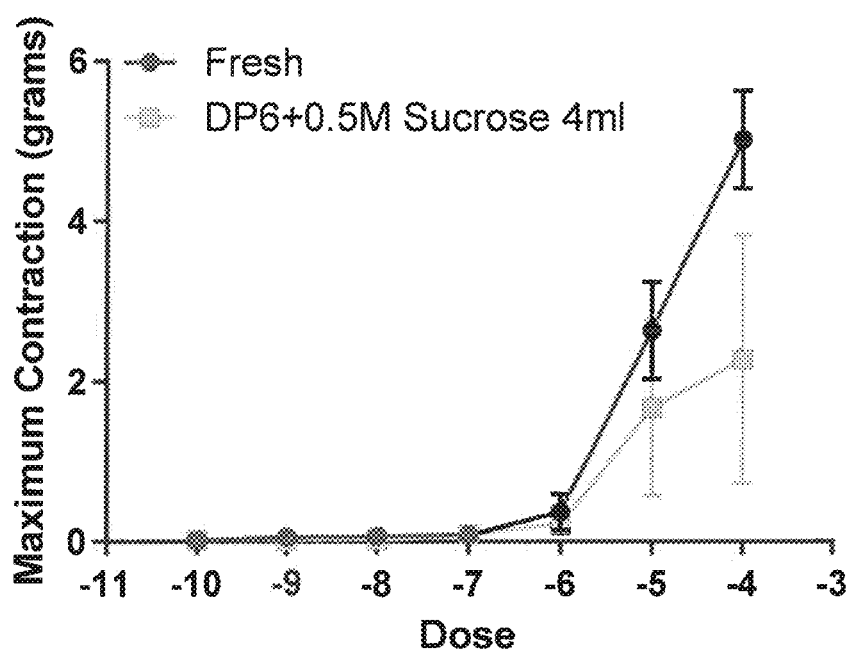

A further series of experiments was conducted with a 0.5M sucrose DP6 formulation with blood vessels using a device called a Cryomacroscope (used to visualize events during cryopreservation). The results are shown in FIG. 2 (Contractile responses of fresh and vitrified rabbit carotid arteries, (top) Norepinephrine and Phenylephrine (lower) dose response curves).

The above study was performed on 4 mL samples using convection warming without nanowarming. Preparation, vitrification and rewarming was performed as previously indicated. The blood vessels were cut into 2 mm rings for testing. The artery samples preserved with DP6 supplemented with 0.5M sucrose yielded greater than 90% viability by alamarBlue using methods described above in the first set of experiments (data not shown). The samples were also checked for smooth muscle function and excellent responses to two contractile drugs were observed, as seen in FIG. 2.

Methods

Blood Vessel Physiology:

Two-mm rings of fresh and ice free cryopreserved blood vessels were prepared for vascular physiology studies to document the function of rabbit femoral artery rings in a Radnoti organ bath system using a panel of constrictive drugs. Isometric contractile tensions were measured after addition of increasing concentrations of each drug using methods previously employed. The physiology results were expressed as grams tension/mg tissue dry weight.

3rd Set of Experiments

Figure 3:
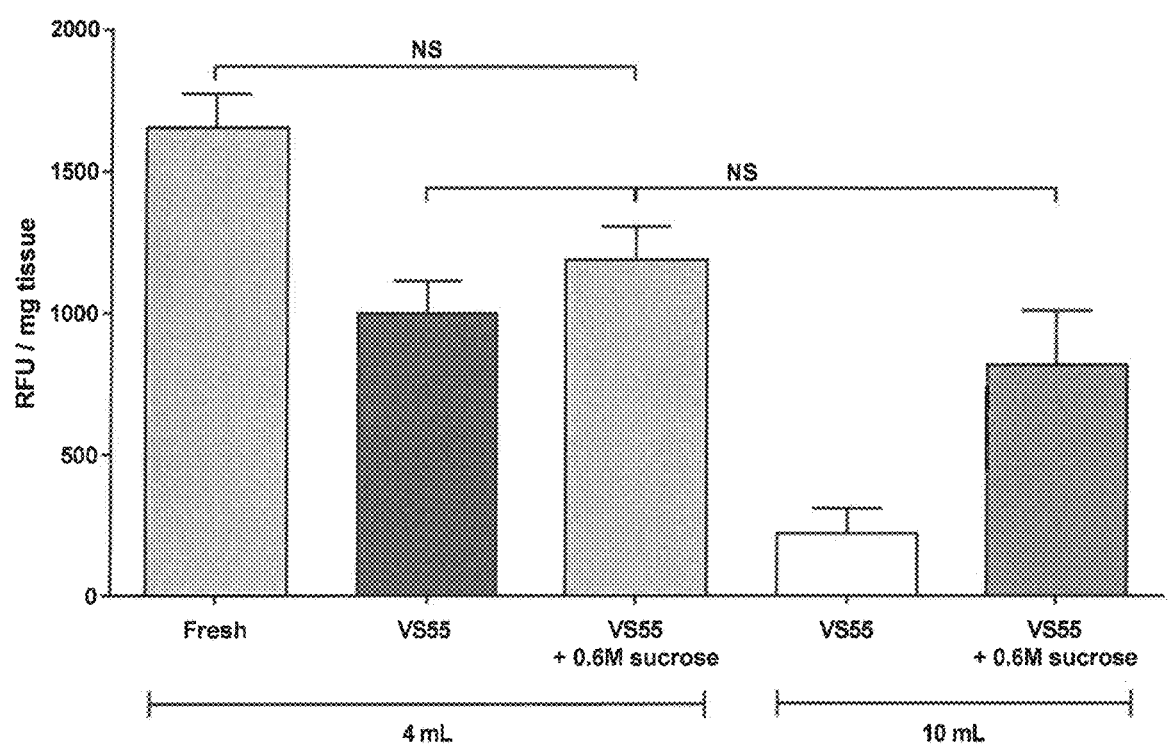
FIG. 3 is an illustration of the data obtained with respect to porcine femoral artery comparison of 4 and 10 mL samples of VS55±0.6M sucrose (alamarBlue assay).
Figure 4:
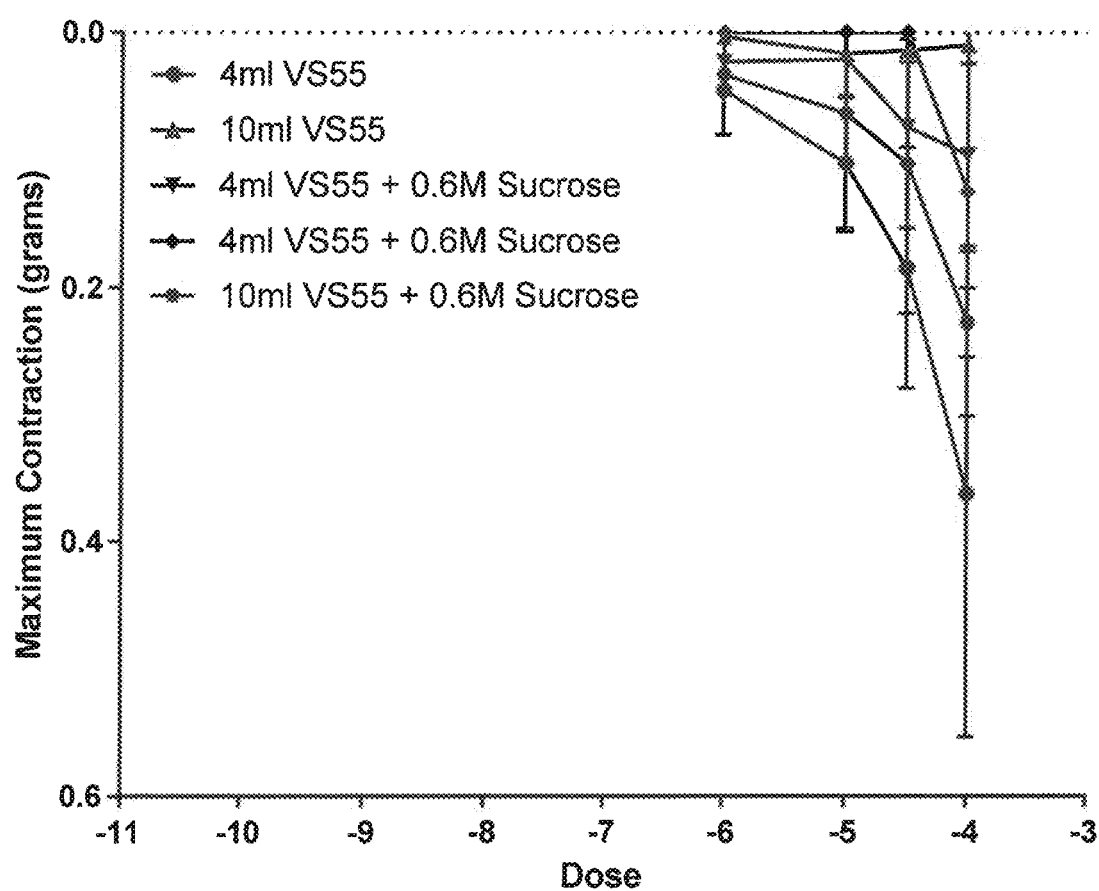
FIG. 4 is an illustration of the data obtained with respect to porcine smooth muscle relaxation induced by sodium nitroprusside after pre-contraction (physiology assay).

Pig femoral artery cryopreservation was performed in VS55±0.6M sucrose at 4 and 10 mL cellular material volumes. Significant preservation was demonstrated in all formulations at 4 mL, whereas at 10 mL the VS55 without sucrose demonstrated low viability. In contrast, the sucrose supplemented formulations demonstrated preservation of viability by both the alamarBlue (FIG. 3; porcine femoral artery comparison of 4 and 10 mL samples of VS55±0.6M sucrose, where tissue rings were assessed using the alamarBlue metabolic assay) and physiology assays (FIG. 4; porcine smooth muscle relaxation induced by sodium nitroprusside after pre-contraction, where VS55 alone works well for a 4 mL sample, but fails at 10 mL sample, and sucrose supplementation preserves the functionality (relaxation) at 10 mL volume sample) employed. These results demonstrate that disaccharide supplementation results in tissue survival at large volumes (e.g., 10 mL volume) where unsupplemented VS55 solution (i.e., no disaccharide added) fails (due to ice formation with loss of tissue viability). Similar results were obtained for two contractile drugs.

The methods used here were the same as in the earlier examples using convection warming.

4th Set of Experiments

Figure 5:
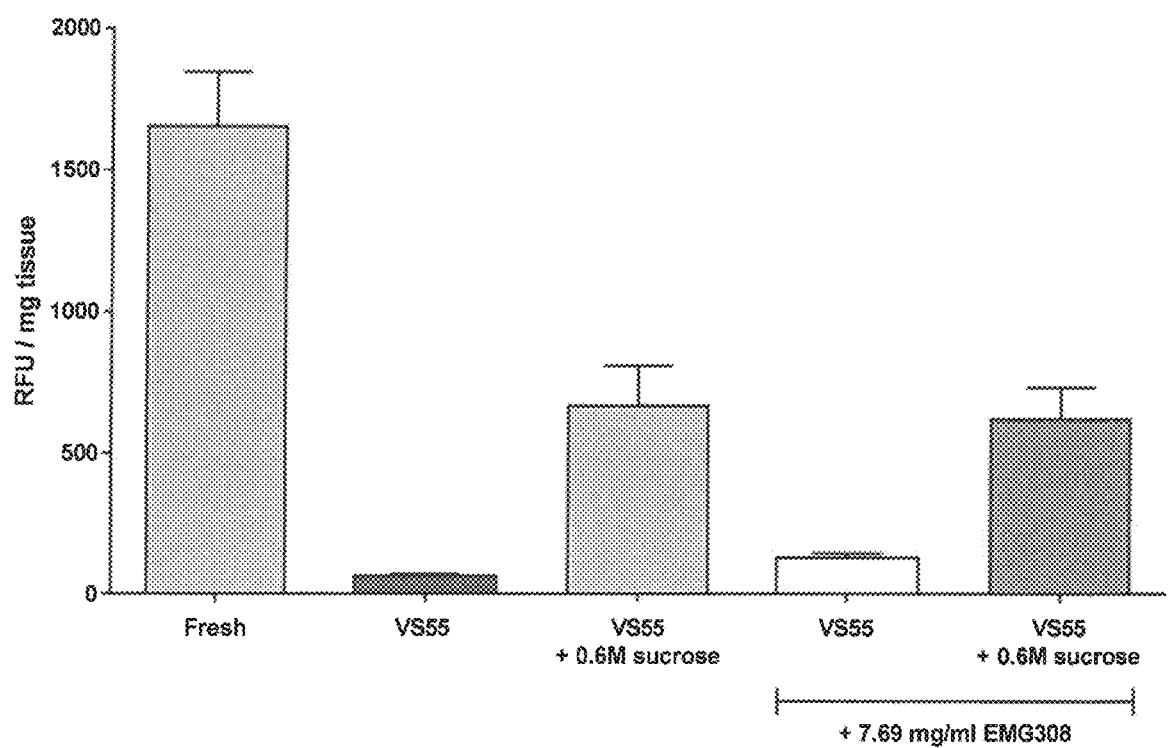
FIG. 5 is an illustration of the data obtained with respect to rabbit thoracic aorta samples that were vitrified in 30 mL volumes of VS55 with or without 0.6M sucrose with or without nanoparticles for comparison of convection versus nanowarming.

Rabbit thoracic aorta samples were vitrified in 30 mL volumes of VS55 with or without 0.6M sucrose with or without nanoparticles for comparison of convection versus nanowarming. The results are set forth in FIG. 5 (30 mL rabbit thoracic aorta results demonstrating improved outcomes with sucrose supplementation using either convection (middle bar) or nanowarming (far right bar)).

The methods were as described for earlier examples regarding addition of cryoprotectants and cooling. However, in this experiment we compared convection warming and nanowarming. Nanowarming was performed after at least 24 h at −130° C. The samples were vitrified with 7.69 mg/ml Fe nanoparticles (EMG-308, Ferrotec) and the samples were inserted into the coil of an inductive heater for rewarming. More specifically we employed a 6.0 kW terminal, 150-400 kHz, EASYHEAT 5060LI solid state induction power supply with a remote work head and custom multi-turn helical coil with 6-7 turns to create a 35 kA/m magnetic field in the center. Good results (just under 50% viability) were achieved with either convection heating or nanowarming (conducted as described in U.S. Patent Application Publication No. 2016/0015025) as long as sucrose was present in the vitrification solution. VS55 without sucrose performed poorly due to ice formation that was observed in the rewarming process.

5th Set of Experiments

Figure 6A:
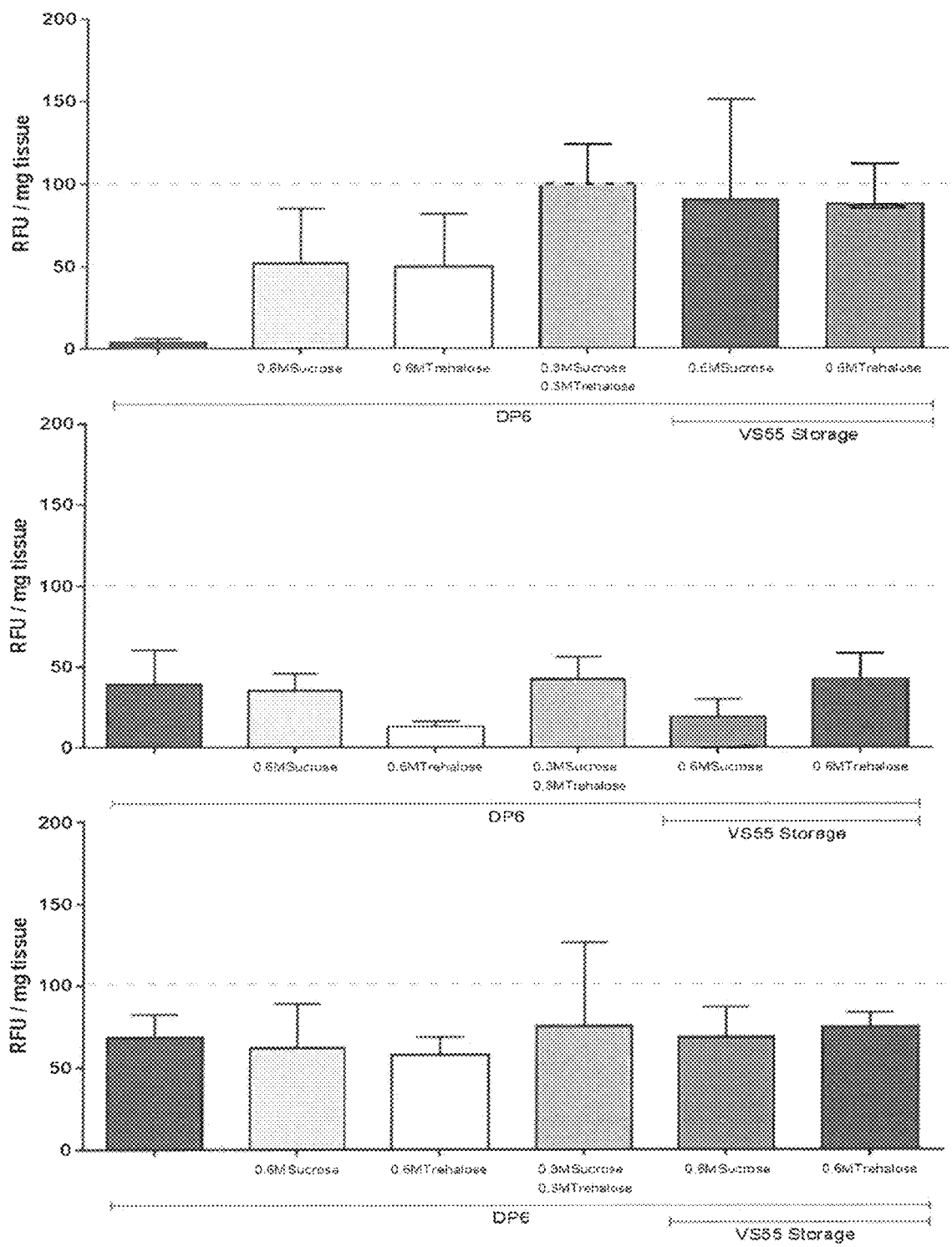
FIGS. 6A and 6B is an illustration of the data obtained with respect to a comparison of the viability of heart valve tissues in which intact heart valves were preserved in 30 mL cryoprotectant volumes and rewarmed by either convection or nanowarming methods.
Figure 6B:
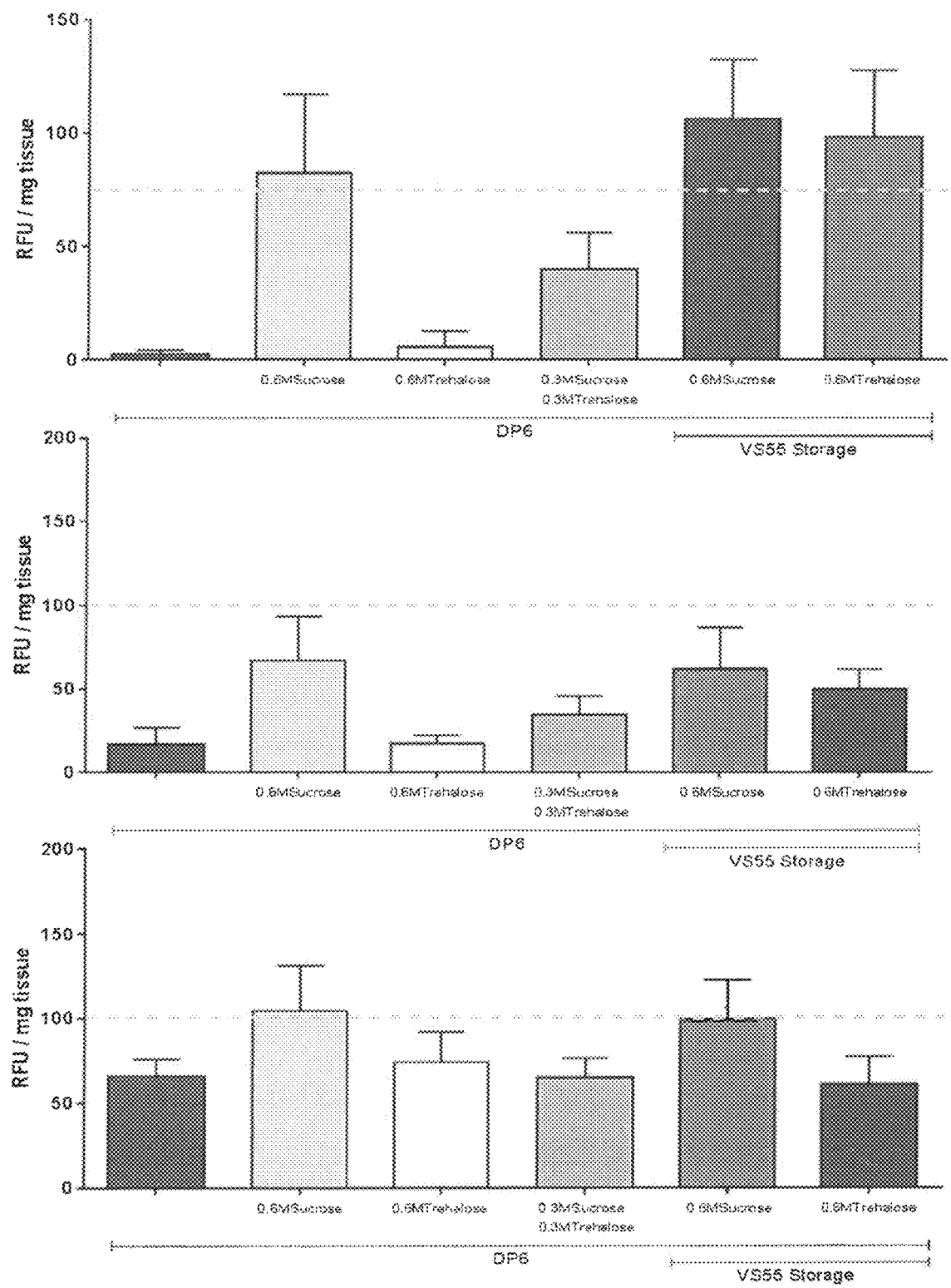

In this series of experiments (the results of which are illustrated in FIG. 6A and FIG. 6B), the viability of heart valve tissues in which intact heart valves were preserved in 30 mL cryoprotectant volumes and rewarmed by either convection or nanowarming methods are compared.

Three tissue samples were taken from each leaflet and associated pulmonary artery and cardiac muscle for a total of 9 samples of each tissue type from each valve. The ice-free vitrification and rewarming procedures were performed as previously described except that a stepwise addition of DP6 was employed with sucrose or trehalose in the last step. In some cases the DP6+sugar step was followed by immersion in VS55+sugar at −10 C followed by immediate vitrification. It should be noted that in this experiment, as also observed in FIG. 1, DP6 alone results in good cardiac muscle cell viability in spite of the freezing that occurs with DP6, however in this experiment two cryopreservation groups achieved control values (FIG. 6B, bottom) after addition of sucrose.

With respect to the data shown in FIG. 6A and FIG. 6B, individual porcine heart valves were loaded with DP6 and then cryopreserved in either DP6 alone, DP6 with either 0.6M trehalose, 0.6M sucrose or a mixture of 0.3M sucrose and 0.3M trehalose, or transferred at the last moment from DP6 with sugar to VS55 with the same sugar. The total volume of tissue and solution was at least 30 mLs. The results from top to bottom are for leaflet, then conduit and finally cardiac muscle. The results in FIG. 6A are for convection warming and the results in FIG. 6B are after nanowarming (n=9). The results are expressed as the mean±1 standard error in percent of untreated control heart valve tissues.

These results demonstrate that DP6 (3.0M dimethylsulfoxide plus 3.0M in EuroCollins Solution) with 0.6M sucrose results in excellent preservation of all three tissue components in heart valves, particularly after nanowarming. Several other treatment groups including loading with DP6 and then transferring to VS55 with either sucrose or trehalose also improved viability after either convection warming or nanowarming. There was a tendency for treatment groups with sucrose to be better than with trehalose.

The above results (FIGS. 1-6) combine to demonstrate that the use of sugars, such as disaccharides, e.g., sucrose and trehalose, with VS55 and more dilute cryoprotectant formulations (DP6, FIG. 6) result in unexpected improved outcomes of ice-free vitrification. These sugars help during both convection and rapid warming with inductive heating of magnetic nanoparticles but it appears that high sucrose and trehalose formulations do not need rapid warming (FIG. 7).

The use of sugars, such as disaccharides, e.g., sucrose and trehalose, permits preservation of large volume samples and slow warming with less risk of ice formation and increased post-rewarming viability.

Storage of VS55 with a range of trehalose and sucrose concentrations demonstrates freedom from ice formation at −80 C for 1 week. In this experiment 30 mL samples of VS55 with increasing concentrations of sugars were placed in 50 mL plastic tubes and stored in a −80 C mechanical storage freezer for 7 days. The tubes were checked daily for ice formation. The tubes demonstrated ice in a sugar concentration dependent manner with the highest concentrations (such as in a range of from 0.5-0.6M) not showing ice formation after 8 days, FIG. 7 shows the tubes after 1 and 7 days of storage. After one day 0.4 to 0.6M trehalose and 0.5-0.6M sucrose were free of ice, while after 7 days 0.5-0.6M trehalose and 0.6M sucrose groups were free of ice. Lower concentrations of these sugars may still be used for ice-free vitrification but more rapid cooling and warming will be needed because the risk of ice formation will be greater and nanowarming rather than convection warming may be needed.

Figure 7:
FIG. 7 is an photograph showing the tubes after 1 and 7 days of storage and ice formation in VS55 supplemented with sugars at −80° C. (Top left: VS55 with 0-0.6M sucrose at 24 hours; Top right: VS55 with 0-0.6M trehalose at 24 hours; Bottom left: VS55 with 0-0.6M sucrose at 7 days; and Bottom right: VS55 with 0-0.6M trehalose at 7 days).

Specifically, FIG. 7 is photograph illustrating the ice formation in VS55 supplemented with sugars at −80° C.:

Top left: VS55 with 0-0.6M sucrose at 24 hours; Top right: VS55 with 0-0.6M trehalose at 24 hours. At this time point the VS55 supplemented with either 0-0.4M sucrose or 0-0.6M trehalose demonstrated ice (white) formation. Higher concentrations were clear without ice. Bottom left: VS55 with 0-0.6M sucrose at 7 days; and Bottom right: VS55 with 0-0.6M trehalose at 7 days. After a week at −80° C. the highest concentrations of sugars are still free of ice.

Incorporation of sugars, such as disaccharides, e.g., sucrose and trehalose, in to such ice-free vitrification formulations permits relatively slow cooling and warming rates (such as on the order of hours or days) to be used without ice formation and loss of cell/tissue viability. Additionally, both convection warming and nanowarming methods may be used in the methods of the present disclosure with the formulations described herein. Rapid warming methods, such as nanowarming methods may still be desired because at rapid warming rates there is less opportunity for cryoprotectant exposure induced cytotoxicity. These observations also suggest that other cryoprotectant formulations with sugars can be developed that have even less risk of cryoprotectant cytotoxicity.

All literature and patent references cited throughout the disclosure are incorporated by reference in their entireties. Although the preceding description has been described herein with reference to particular means, materials and embodiments, it is not intended to be limited to the particulars disclosed herein; rather, it extends to all functionally equivalent structures, methods and uses, such as are within the scope of the appended claims. Furthermore, although only a few example embodiments have been described in detail above, those skilled in the art will readily appreciate that many modifications are possible in the example embodiments without materially departing from the disclosure of ICE-FREE PRESERVATION OF LARGE VOLUME TISSUE SAMPLES FOR VIABLE, FUNCTIONAL TISSUE BANKING. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method for preserving living large volume cellular material, comprising:
    exposing the cellular material to a cryoprotectant formulation containing from 0.5 M to 2 M of at least one sugar selected from trehalose and/or sucrose, wherein the cellular material is obtained from intestine, pancreas, testes, placenta, thymus, adrenal gland, arteries, veins and lymph nodes,
    subjecting the cellular material to a preservation protocol in which ice-induced damage to the cellular material does not occur, wherein the preservation protocol includes a cooling protocol, a storage phase, and a warming protocol, where during the cooling protocol a continuous controlled rate of about −0.1 to about −2° C. per minute is used to cool the cellular material from a point of initiation temperature to −80° C. or lower, the point of initiation temperature being in a range of from about +4 to −30° C., and after completion of the preservation protocol, obtaining a cryopreserved cellular material; wherein
    the cellular material has a volume greater than 4 mL.

2. The method of claim 1, wherein the cellular material has a volume greater than 10 mL.

3. A method for increasing production yield of viable cryopreserved cellular material, comprising:
    exposure of a large volume cellular material to a cryoprotectant, the cryoprotectant containing from 0.5 M to 2 M of at least one sugar selected from trehalose and/or sucrose, wherein the cellular material is obtained from intestine, pancreas, testes, placenta, thymus, adrenal gland, arteries, veins and lymph nodes, for a predetermined amount of time to form a cryopreservation formulation;
    subjecting the cryopreservation formulation to a preservation protocol comprising cryopreservation at a cryopreservation temperature of about −80° C. or lower, wherein
    the preservation protocol includes a cooling protocol, a storage phase, and a warming protocol, where during the cooling protocol a continuous controlled rate of about −0.1 to about −2° C. per minute is used to cool the cellular material from a point of initiation temperature to the cryopreservation temperature of about −80° C. or lower, and the point of initiation temperature is in a range of from about +4 to −30° C.; and
    after completion of the preservation protocol, recovering the cryopreserved cellular material; wherein a cell viability (%) of the recovered cryopreserved cellular material is at least 60% and the cellular material has a volume greater than 4 mL.

4. The method of claim 1, wherein the preservation protocol includes a vitrification strategy that limits the growth of ice during cooling and warming such that ice-induced damage does not occur during the preservation protocol.

5. The method of claim 1, wherein the at least one sugar is trehalose.

6. The method of claim 1, wherein subjecting the cellular material to a preservation protocol comprises:
    stepwise cryoprotectant addition to the cryoprotectant formulation to achieve a final cryoprotectant formulation with a cryoprotectant concentration and/or at least one sugar concentration effective to avoid ice-induced damage to the cellular material.

7. The method of claim 1, wherein
    the preservation protocol further comprises cooling the cellular material in a cryoprotectant formulation containing at least one sugar,
    a further cryoprotectant is added to the cryoprotectant formulation prior or during cooling, the further cryoprotectant being different from the sugar, and
    the cryoprotectant formulation contains the at least one sugar and further cryoprotectant at a concentration of from 6.5 to about 11 M.

8. The method of claim 7, wherein the further cryoprotectant is selected from the group consisting of acetamide, agarose, alginate, alanine, albumin, ammonium acetate, antifreeze proteins, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, ice recrystalization inhibitors, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

9. The method of claim 1, wherein the cellular material is selected from human tissues, the human tissues being selected from the group consisting of arteries and veins.

10. The method of claim 1, wherein a cell viability (%) of the cellular material after completion of the preservation protocol is at least 60%.

11. The method of claim 1, wherein the medium does not contain DMSO, formamide and/or propylene glycol.

12. The method of claim 3, wherein the warming protocol includes a two-step warming procedure in which, during a first warming step, the cellular material that was stored is rewarmed in a first environment at a first warming temperature that is greater than the cryopreservation temperature, and then, in a second warming step, the cellular material is further rewarmed in a second environment at a second warming temperature that is greater than the first warming temperature used in the first warming step; wherein
the first environment is a gaseous atmosphere,
the first warming temperature is in the range of from about −15° C. to about −30° C., and
the second warming temperature is in a range of from about 35° C. to about 45° C.

13. The method of claim 12, wherein the cellular material is selected from mammalian tissues, the mammalian tissues being selected from the group consisting of arteries and veins.

14. The method of claim 12, wherein the cell viability (%) of the recovered cryopreserved cellular material is at least 80%.

15. A method for preserving living large volume cellular material, comprising:

exposing the cellular material to a cryoprotectant formulation containing from 0.5 M to 2 M of at least one sugar selected from trehalose and/or sucrose,
subjecting the cellular material to a preservation protocol in which ice-induced damage to the cellular material does not occur, wherein the preservation protocol includes a cooling protocol, a storage phase, and a warming protocol, where during the cooling protocol a continuous controlled rate of about −0.1 to about −2° C. per minute is used to cool the cellular material from a point of initiation temperature to −80° C. or lower, and the point of initiation temperature is in a range of from about +4 to −30° C., and after completion of the preservation protocol, obtaining a cryopreserved cellular material; wherein
the cellular material is a heart valve.

16. The method of claim 15, wherein the heart valve is obtained from a mammalian source.

17. The method of claim 15, wherein
the exposing the cellular material to a cryoprotectant formulation containing from 0.5 M to 2 M of at least one sugar selected from trehalose and/or sucrose comprises immersing the heart valve in the cryoprotectant formulation containing the at least one sugar, and
the heart valve is not contacted via perfusion with a cryoprotectant-containing solution before, during or after the exposure to the cryoprotectant formulation containing the at least one sugar.

18. The method of claim 1, wherein
the exposing the cellular material to a cryoprotectant formulation containing from 0.5 M to 2 M of at least one sugar selected from trehalose and/or sucrose comprises immersing the cellular material in the cryoprotectant formulation containing the at least one sugar, and
the cellular material is not contacted via perfusion with a cryoprotectant-containing solution before, during or after the exposure to the cryoprotectant formulation containing the at least one sugar.

19. The method of claim 1, wherein during the cooling protocol the continuous controlled rate is about −0.1 to about −0.5° C. per minute.

20. The method of claim 1, wherein the entire preservation protocol has a duration in a range of from at least 5 days up to about 2 months.

* * * * *